US006768784B1

(12) United States Patent
Green et al.

(10) Patent No.: US 6,768,784 B1
(45) Date of Patent: Jul. 27, 2004

(54) X-RAY IMAGE ENHANCEMENT

(75) Inventors: Donald T. Green, Madison, OH (US); Pieter Gerhard Roos, Bainbridge, OH (US); Kurtis M. Molter, North Royalton, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 192 days.

(21) Appl. No.: 10/045,364

(22) Filed: Nov. 7, 2001

(51) Int. Cl.[7] .................................................. H05G 1/64
(52) U.S. Cl. ....................................................... 378/62
(58) Field of Search .............................. 378/41, 42, 44, 378/45, 51, 62

(56) References Cited

U.S. PATENT DOCUMENTS 5,117,114 A    5/1992    Street et al.
5,319,206 A    6/1994    Lee et al.
5,331,179 A    7/1994    Lee et al.
5,574,764 A    11/1996   Granfors et al.
5,917,882 A    6/1999    Khutoryansky et al.
6,108,403 A    8/2000    Cooper et al.

FOREIGN PATENT DOCUMENTS

EP        0 648 466 A1       4/1995

Primary Examiner—Eric S. McCall
(74) Attorney, Agent, or Firm—Thomas M. Lundin

(57) ABSTRACT

A fluoroscopic imaging apparatus is provided. The apparatus includes an x-ray source for projecting x-rays through a subject. The x-ray source has a voltage and a current associated therewith. The apparatus also includes an x-ray detector for detecting radiation which has passed through the subject and a monitor for displaying an image indicative of the detected radiation. The image defines a field of view. In addition, the fluoroscopic imaging apparatus includes an operator interface for selecting a region of interest within the field of view. In response to image data within the region of interest, an image of the region of interest can thereafter be enhanced.

18 Claims, 2 Drawing Sheets

X-RAY IMAGE ENHANCEMENT

BACKGROUND

The present invention relates to the medical imaging arts. It finds application in conjunction with x-ray systems and will be described with particular reference to fluoroscopic imaging systems. However, it should be appreciated that the present invention may also find application in conjunction with other types of imaging systems and applications.

X-ray systems are often used to perform medical imaging and examinations. Examples of x-ray systems suitable for such applications include analog and digital fluoroscopy, spot imaging, and planar tomography. In such systems, an x-ray source is disposed on one side of a patient and an x-ray detector is disposed on the other side of the patient. The x-ray detector converts x-rays which have passed through the patient into secondary carriers (e.g. visible light) which are subsequently converted to signals for image processing.

With particular reference to fluoroscopic imaging systems, these systems can produce substantially instantaneous and continuous (i.e. real-time) images that are usefwil for guiding a procedure, searching through a body section, or observing a dynamic function.

Analog fluoroscopic x-ray systems typically include an x-ray source, an image aintensifier tube, an optical image distribution system, and a video system containing a camera, monitor, and associated electronics. The x-ray source directs a continuous beam of radiation through a subject under examination. A pattern of radiation emerges from the subject and passes through the image intensifier tube which converts the radiation into a pattern of light representing an image of the subject. The pattern of light then passes through the distribution system, is directed to the video camera, and is subsequently shown on the monitor.

Digital fluoroscopic systems typically include a flat panel image detector which includes a scintillator layer and an addressable silicon detector array. Each of the elements in the array convert the light detected by it into an electrical charge. This charge is converted into a corresponding digital signal for further processing and storage. One such image detector is disclosed in U.S. Pat. No. 5,117,114. Other digital fluoroscopic image detectors do not include a scintillator layer, the detectors convert incident radiation into an electrical charge using a selenium photoconductor layer on top of a microcapacitor matrix. Such detectors are disclosed, for example in U.S. Pat. Nos. 5,331,179 and 5,319,206. Still other image detectors are known in the art and are readily available.

Regardless of the type of imaging system, in order for an x-ray system to produce images, the x-ray source must produce x-ray radiation at a level such that at least a portion of the x-rays pass through the subject and are received by the x-ray detector. As the x-rays enter the subject, they are attenuated by the tissues of the subject. The more dense the tissue, the greater the attenuation of the x-rays. The x-rays are attenuated during this penetrating process as a function of the density of the tissue through which they pass by the process of absorption of energy by the tissues. As the x-rays emerge from the other side of the subject, the energy that is still retained is, therefore, a function of the density of the tissues that were penetrated as well as the initial energy of the x-rays generated by the x-ray source. Accordingly, increasing the energy of the x-ray source increases the ability of the x-rays to penetrate the subject and subsequently produce x-ray images. In cases where the quality of the images is poor due to excessive x-ray penetration, the energy can be reduced to a desired level.

One difficulty associated with producing x-ray images is that x-rays incident on the x-ray detector are either of an intensity level which is too high or too low, thereby resulting in reduced image quality. Therefore, during x-ray imaging, an intensity level of x-rays reaching the x-ray detector can be monitored to assure that the overall intensity of x-rays received by the x-ray detector is satisfactory to produce an image of diagnostic quality. The intensity of the x-rays received by the x-ray detector can be measured in terms of exposure. If it is determined that the x-ray detector is not receiving satisfactory exposure to x-rays, a signal can be sent to the x-ray source to adjust either one, or both, of the number of x-rays and the energy of the x-rays produced by the x-ray source.

In addition, despite the control of the x-ray source, it is possible that desired quality of the images cannot be achieved. This may be due to inadequate brightness or contrast within a region of interest. More specifically, image quality is substantially based on the ability to see contrast between certain types of anatomy. Typically, data from an x-ray detector are mapped, pixel by pixel, to a display scale consisting of, for example, a gray scale of 256 steps from black to white. Detected x-rays which are mapped into a central portion of the 256 steps will typically provide sufficient contrast to readily distinguish among different anatomy within a region of interest whereas pixels mapped within a small range of the gray scale or near the upper or lower bounds of the gray scale will typically fail to exhibit enough image contrast to properly distinguish and interpret such portions of the image. This can occur when the x-ray detector pixels cause there to be a wide range of x-ray data mapped in most of the gray scale steps thereby causing the range of pixels holding the image data of the region of interest to be mapped to a region having lower overall gray scale contrast.

Manipulating the x-ray intensity and processing the images to achieve high quality images can be difficult, however. For example, it is difficult to know whether, and to what extent, to control the radiation energy, radiation dose, and image processing parameters. Even if the user is skilled, this process can be time consuming and difficult. It is therefore desirable to automate such controls.

U.S. Pat. No. 5,574,764 obtains images by adjusting the x-ray intensity and image display brightness level. This is accomplished by feeding back an average pixel brightness value within a region of interest to the x-ray source to control the x-ray exposure. The average pixel value is also used to determine an image processing scaling factor to maintain a desired brightness level in situations where the necessary x-ray exposure cannot be attained.

The utility of this approach is limited where a region of interest within the field of view of the x-ray system is too dark or bright and adjusting the x-ray source controls and the image processing parameters is insufficient to adequately display the region of interest. In U.S. Pat. No. 5,574,764, the region of interest is fixed in both location and size and cannot be changed interactively by the user during image acquisition. This is problematic when, for example, the portion of a subject's anatomy that the user wishes to view falls outside the initial region of interest or is too small with respect to the size of the region of interest to distinguish.

It is therefore desirable to have automated x-ray source and image processing controls that respond to the image characteristics of an operator-defined region of interest. It is also accordingly desirable that the operator can select such a region of interest interactively during real-time imaging.

SUMMARY

Embodiments of the present invention address these matters, and others.

In accordance with one aspect of the present invention, a fluoroscopic imaging apparatus is provided. The imaging apparatus includes an x-ray source for projecting x-rays through a subject, the x-ray source having a voltage and a current associated therewith and an x-ray detector for detecting radiation which has passed through the subject. The apparatus also includes a monitor for displaying an image indicative of the detected radiation and the image defining a field of view. In addition, the apparatus includes an operator interface for selecting a region of interest within the field of view and enhancement means for enhancing, in response to image data within the region of interest, a subsequent image of the region of interest.

In accordance with a more limited aspect of the present invention, the enhancement means includes an image processor which generates a brightness histogram of pixels within the region of interest, an automatic exposure controller which, in response to the brightness histogram, adjusts at least one of the voltage and current of the x-ray source, and an automatic brightness controller which, in response to the brightness histogram, generates a lookup table for mapping pixels generated by the fluoroscopic imaging apparatus to a display scale for displaying the pixels on the monitor.

In accordance with a more limited aspect of the present invention, the display of the region of interest has a brightness range and the brightness range is substantially constant.

In accordance with a more limited aspect of the present invention, the automatic brightness controller includes a look-up table which maps a minimum brightness value from within the region of interest to black on the monitor and which maps a maximum brightness value from within the region of interest to white on the monitor.

In accordance with a more limited aspect of the present invention, the operator interface includes a pointing device for selecting a size and a location of the region of interest.

In accordance with a more limited aspect of the present invention, the position of the pointing device is overlaid on the image.

In accordance with a more limited aspect of the present invention, the region of interest is less than or equal to the field of view in size.

In accordance with a more limited aspect of the present invention, the region of interest can be updated by the operator during image acquisition.

In accordance with another aspect of the present invention, a fluoroscopic imaging apparatus for enhancing, in real-time, a display of a region of interest within a fluoroscopic image is provided. The apparatus includes an x-ray source for projecting x-rays through a subject, the x-ray source having a voltage and a current associated therewith for controlling the projected x-rays, an x-ray detector for detecting radiation which has passed from the x-ray source through the subject, display means for displaying real-time video images indicative of the detected radiation on a monitor, and a pointing device by which an operator can select a region of interest from within the video images. The apparatus also includes an image processor for generating a histogram of image data of the region of interest, an automatic exposure controller for controlling at least one of the x-ray source voltage and the x-ray source current in response to the histogram of the region of interest, and an automatic brightness controller for mapping the image data of the region of interest to a display scale of the monitor in response to the histogram of the region of interest.

In accordance with a more limited aspect of the present invention, the histogram is generated using all pixels from within the region of interest.

In accordance with a more limited aspect of the present invention, the operator can interactively select the size and location of the region of interest using the pointing device.

In accordance with a more limited aspect of the present invention, the pointing device has a position which is overlaid on the real-time video images displayed on the monitor.

In accordance with a more limited aspect of the present invention, the display of the region of interest has a brightness range and the brightness range is substantially constant between successive displays of the region of interest.

In accordance with another aspect of the present invention, a method of fluoroscopic imaging is provides. The method includes the steps of projecting x-rays through a subject using an x-ray source, the x-ray source having a voltage and current associated therewith, detecting radiation which has passed through the subject, displaying on a monitor an image indicative of the received radiation, the image defining a field of view, and displaying borders of a region of interest, the region of interest being within the field of view and being defined by an operator and having a brightness and contrast associated therewith. The method also includes generating a brightness histogram of the image data within the region of interest, adjusting at least one of the x-ray source voltage and current in response to the brightness histogram of the region of interest whereby the display of the region of interest is thereafter enhanced, and adjusting at least one of the brightness and contrast of the region of interest in response to the histogram of the region of interest whereby the display of the region of interest is thereafter enhanced.

In accordance with a more limited aspect of the present invention, the step of generating a histogram includes using all pixels from within the region of interest.

In accordance with a more limited aspect of the present invention, the step of adjusting at least one of the brightness and contrast of the region of interest includes mapping a minimum brightness from within the region of interest to black on the monitor and mapping a maximum brightness from within the region of interest to white on the monitor.

In accordance with a more limited aspect of the present invention, the borders of the region of interest are superimposed on the display of the field of view.

One advantage of the present invention is that it provides a fluoroscopic imaging apparatus that controls the x-ray source and the lookup table applied to the images as the images are displayed.

Another advantage of the present invention is that is controls the x-ray source and lookup table in response to an operator defined region of interest.

Another advantage of the present invention is that the region of interest can be selected interactively and in real-time during image acquisition.

Another advantage of the present invention is that the region of interest can be automatically enhanced.

Still other advantages and benefits of the invention will become apparent to those skilled in the art upon a reading and understanding of the following detailed description.

DRAWINGS

The invention may take form in various components and arrangements of components, and in various steps and arrangements of steps. The drawings are only for purposes of illustrating a preferred embodiment and are not to be construed as limiting the invention.

DESCRIPTION

Figure 1:
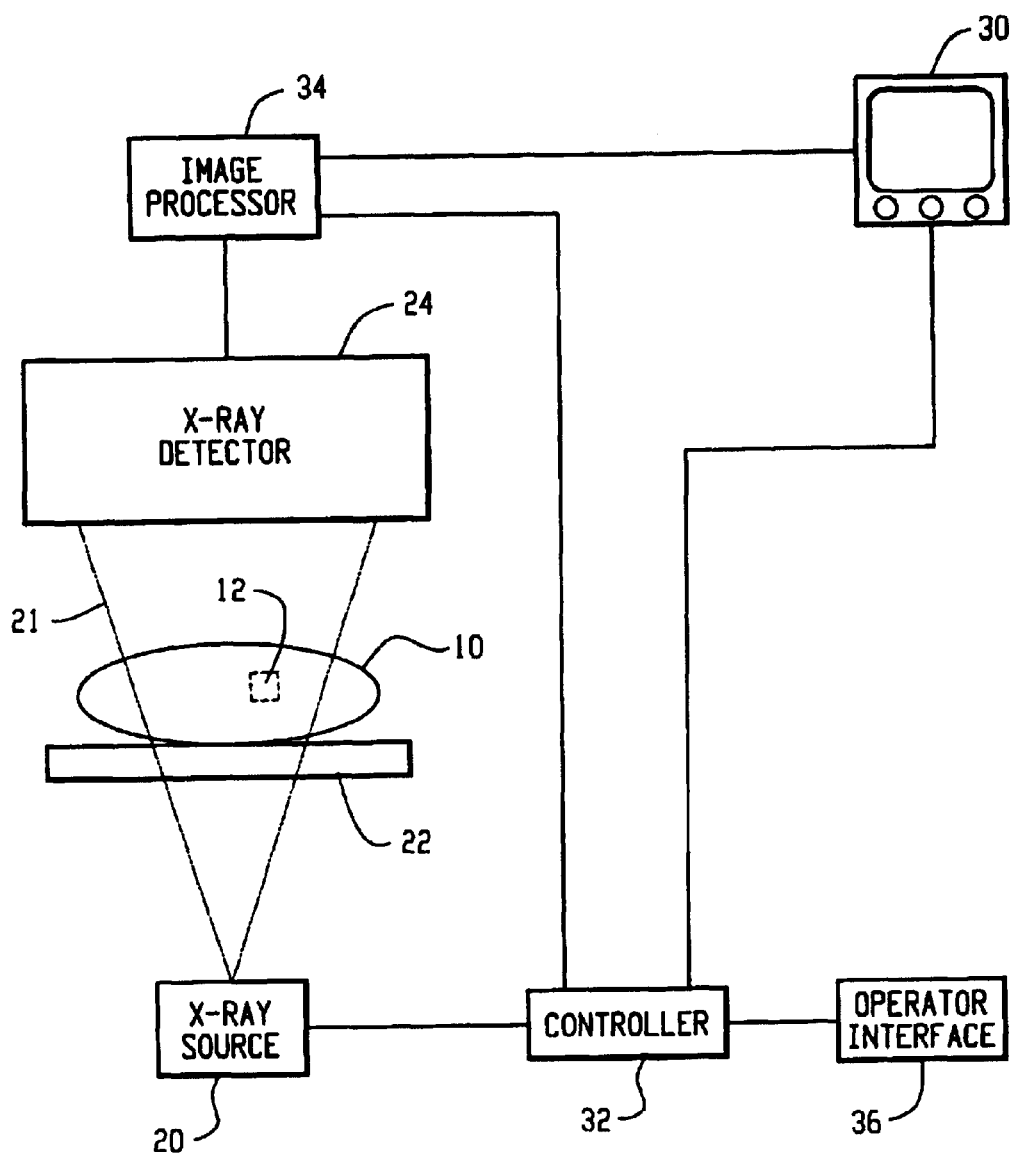
FIG. 1 is an illustration of a fluoroscopic x-ray system.

An example of a fluoroscopic imaging system is shown in FIG. 1. The system includes an x-ray source 20 positioned in relation to an examination table 22 such that an x-ray beam 21 generated by the x-ray source 20 passes through a region of interest 12 of a subject 10 under investigation. An x-ray detector 24 is disposed opposite the x-ray source 20 such that x-rays passing through the subject 10 are received by the x-ray detector 24. It is to be appreciated that the x-ray source 20 and x-ray detector 24 can be positioned in alternate locations relative to the subject 10 as long as the x-ray detector is located so as to receive the x-rays generated by the x-ray source after they have passed through the subject 10, and in particular, through the region of interest 12.

In one embodiment, the x-ray detector 24 includes an intensifier tube which converts x-rays into light and intensifies the light in the process. In this embodiment, a distributor is coupled to the intensifier tube. The distributor receives the intensified light from the intensifier tube and directs the light to a camera and is subsequently shown on a monitor. In addition, the signals can be digitized for each of a plurality of pixels, as is known in the art, for further signal processing.

In another embodiment, the x-ray detector 24 includes a flat panel image detector which includes a scintillator layer and an addressable silicon detector array. The scintillator layer converts x-rays into light indicative of the x-rays. Elements of the silicon array convert the light produced by the scintillator layer into corresponding electrical signals representing a plurality of pixels for further processing.

In another flat panel image detector embodiment, the x-ray detector 24 includes a solid-state x-ray detector which includes a selenium photoconductor layer on top of a microcapacitor matrix. This photoconductor layer converts x-rays into electrical signals, representing a plurality of pixels, indicative of the x-rays. The pixel data can then be stored and/or further processed as with x-ray systems that utilize other types of x-ray detectors.

It will be appreciated by those skilled in the art that other x-ray detectors could be used in place of those described above.

Continuing with FIG. 1, an image processor 34 is connected to the x-ray detector 24. The image processor 34 processes the pixel data for displaying corresponding images on a video monitor 30, storing the signals on various storage media, or for further processing on a post-processor, as desired.

The image processor 34 includes a histogram generator which generates a histogram of the pixel values within the region of interest 12 from the signals received from the x-ray detector 24. The image processor also includes a processor which processes the signals from the x-ray detector 24 through a lookup table. This process maps the pixel values of the image to display scale, or brightness values, for displaying the image on the monitor 30. In one embodiment, the display scale is a gray scale consisting of 256 steps from black to white. Other embodiments include different numbers of steps as well as colored scales.

A system controller 32, is connected to the x-ray source 20 and controls the radiation parameters of the x-ray beam 21. The controller 32 is also connected to the image processor 34 and monitor 30 for transferring information between the controller and these devices. The controller 32 receives input from an operator interface 36 by which an operator can enter operating parameters for the systemn.

Via the operator interface 36, the operator can enter x-ray parameters to control the x-ray source such as the energy (kV) and current (mA) of the x-rays beam 21 and the time during which the x-ray beam 21 is active. The operator interface 36 also includes a pointing device, such as a computer mouse. The position of the pointing device is recorded on the system controller 32 and is displayed on the monitor 30.

Figure 2:
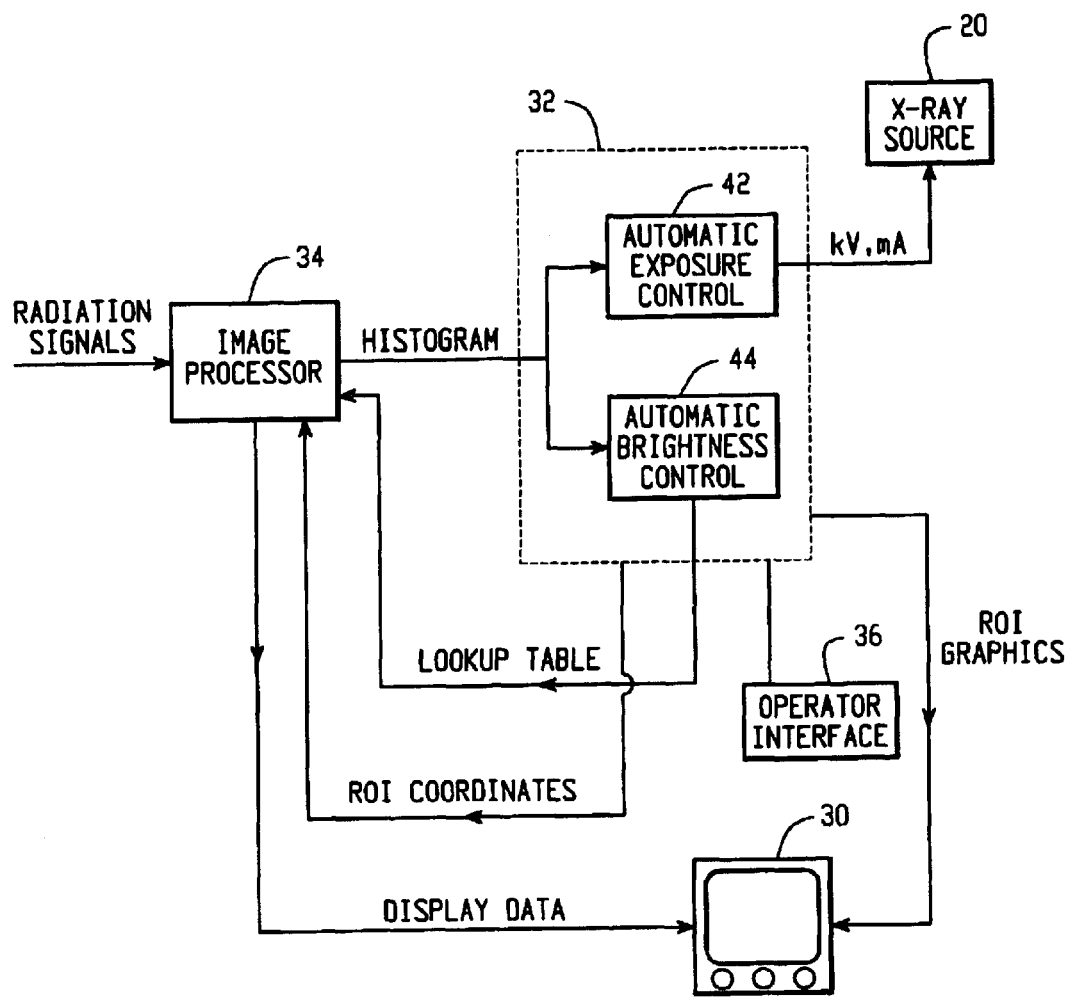
FIG. 2 is a block diagram showing the flow of information in the fluoroscopic system.

With reference to FIG. 2, the controller 32 includes an automatic exposure control 42 which controls the radiation exposure of the subject 10 by regulating the intensity of the x-ray beam 21 generated by the x-ray source 20. More specifically, in response to a given input, the automatic exposure control 42 provides a kilovolt signal and a milliamp signal to the x-ray source 20. The kilovolt signal serves to vary the energy level of the x-rays produced by the x-ray source, while the milliamp signal serves to vary the amount of x-rays produced and emitted by the x-ray source per unit time.

The controller 32 also includes an automatic brightness control 44 which, in response to a given input, controls the brightness and contrast of the display of the images on the monitor 30 through image processing techniques. The image processing techniques include the use of a brightness histogram indicative of the electronic signals generated by the x-ray detector 24 and a lookup table which maps the electronic signals to an appropriate gray scale, or brightness level, for displaying images representing the electronic signals on the monitor 30.

In operation, the subject 10 is placed on the examination table 22 and is positioned relative to the x-ray source 20 so that the region of interest 12 is within the x-ray beam 21 and so that radiation that passes through the subject 10 is received by the x-ray detector 24. Initially, an operator of the system selects an energy level (mV) and current (mA) for the x-ray source 20 and inputs the desired values, as well as other control parameters, into the controller 32 using the operator interface 36. The x-ray source produces an x-ray beam 21 and the resulting x-ray beam enters the subject 10. A pattern of radiation passes through the subject and is received by the x-ray detector 24. The radiation received by the x-ray detector 24 is converted into electronic signals indicative of the received x-rays. These signals are then transmitted as digital pixel values to the image processor 34.

In one embodiment, the image processor 34 initially maps the pixel values according to a default lookup table. The mapped data are then displayed on the monitor 30. The image processor 34 also generates a brightness histogram of the pixel values of the data within a default region of interest. The histogram is passed to the controller 32 for use by the automatic exposure controller 42 and automatic brightness controller 44.

The automatic exposure controller 42 generates a brightness value from the brightness histogram. In one embodiment, this value is the median brightness of the region of interest 12. Using a calibrated relationship between the brightness value of the histogram and the intensity of the x-ray beam 21, the brightness value can be used as feedback for adjusting the kV and mA values of the x-ray source 20 and, in turn, the radiation that the subject 10 receives. For example, if the brightness value is lower than a preset reference value, the overall intensity of the x-ray source 20 is automatically increased. This results in an increase of radiation intensity received by the subject 10, and in turn, an increased brightness within the region of interest 12.

With more specific regard to the automatic exposure controller 42, the brightness value from the brightness histogram can be calculated for each image digitized by the fluoroscopic system. The x-ray intensity parameters (kV and/or mA) can then be adjusted to maintain this brightness value at or near the preset reference value, in closed loop fashion. The calculation of the brightness value and the feedback to the x-ray source 20 can be done by system software or by dedicated digital circuits.

The kV and mA values can be adjusted together or separately. For example, the following methods can be used: 1) keep the kV at a fixed preset value and vary only the mA to achieve the desired brightness value; 2) keep the mA at a fixed preset value and vary only the kV to achieve the desired brightness value; or 3) modify the kV and mA together according to a fixed mathematical relationship. An example of the latter method includes varying kV and mA, in a linear or other relationship, with upper and lower limits in kV, beyond which only the mA is varied.

The automatic brightness controller 44 generates a lookup table for displaying images on the monitor 30 based on the characteristics of the brightness histogram of the data within the region of interest 12. The lookup table from the automatic brightness controller 44 is transmitted to the image processor 34 and signals generated by the x-ray detector 24 are mapped according to the new lookup table and are subsequently displayed on the monitor 30.

In one embodiment, lowest and highest significant brightness values in the brightness histogram of the region of interest 12 are determined. Lookup table parameters are then generated such the lowest significant brightness value maps to black on the monitor 30, the highest brightness value maps to white, and intermediate brightness values map linearly to gray levels in between. Alternate embodiments include mapping intermediate brightness values to gray levels according to a non-linear finction. For example, a function proportional to the logarithm or the gamma of the pixel value could be used. Additionally, a user definable curve could be used. The two extreme points on this curve can, however, still be determined by the lowest and highest significant brightness values in the histogram of the region of interest, such that the display appears at a constant brightness range, despite changes in subject anatomy and x-ray levels.

In one embodiment, the lowest significant brightness value is selected from the points between the 1% and 10% histogram population and the highest significant brightness value is selected from the points between the 90% and 99% histogram population. Alternate embodiments for generating the lookup table include use of more than just the lowest and highest significant brightness values to generate the lookup table.

The process of collecting and displaying image data is repeated continuously and in real-time while the operator views the images on the monitor 30. If there is a region of interest within the displayed image which the operator wishes to see in greater detail, the operator can use the operator interface 36 to select boundaries of the region of interest 12. The position of the operator interface 36 is superimposed over the fluoroscopic images as they are displayed on the monitor 30 so that accurate boundaries of the region of interest 12 can be selected. The display of the region of interest 12 is thereafter enhanced as described below.

The coordinates of the region of interest 12 defined by the operator are input into the image processor 34. The image processor 34 generates a brightness histogram of pixels within the region of interest 12 defined by the operator. The brightness histogram is then input into the automatic exposure and brightness controllers.

As described above, the histogram is used by the automatic exposure controller and the x-ray source 20 is adjusted so that the brightness value of a subsequent brightness histogram of the region of interest 12 is equal to a predetermined value. The histogram is also used by the automatic brightness controller and parameters for the lookup table are generated. The updated lookup table is subsequently used by the image processor 34 and the enhanced image is displayed on the monitor using the updated lookup table.

This process of selecting a region of interest, and enhancing the display of the region of interest, can be repeated as desired by the user.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A fluoroscopic imaging apparatus comprising:
    an x-ray source for projecting x-rays through a subject, the x-ray source having a voltage and a current associated therewith;
    an x-ray detector for detecting radiation which has passed through the subject;
    a monitor for displaying an image indicative of the detected radiation, the image defining a field of view;
    an operator interface for defining a region of interest within the field of view wherein the region if interest is defined by an operator during image acquisition; and
    enhancement means for enhancing, in response to image data within the region of interest, a subsequent image of the region of interest.

2. A fluoroscopic imaging apparatus according to claim 1 wherein the enhancement means comprises:
    an image processor which generates a brightness histogram of pixels within the region of interest;
    an automatic exposure controller which, in response to the brightness histogram, adjusts at least one of the voltage and current of the x-ray source; and
    an automatic brightness controller which, in response to the brightness histogram, generates a lookup table for mapping pixels generated by the fluoroscopic imaging appatus to a display scale for displaying the pixels on the monitor.

3. A fluoroscopic imaging apparatus according to claim 2 wherein the display of the region of interest has a brightness range and the brightness range is substantially constant.

4. A fluoroscopic imaging apparatus according to claim 3 wherein the automatic brightness controller includes a lookup table which maps a minimum brightness value from within the region of interest to black on the monitor and which maps a maxiunum brightness value from within the region of interest to white on the monitor.

5. A fluoroscopic imaging apparatus according to claim 1 wherein the operator interface includes a pointing device for selecting a size and a location of the region of interest.

6. A fluoroscopic imaging apparatus according to claim 5 wherein the position of the pointing device is overlaid on the image.

7. A fluoroscopic imaging apparatus according to claim 1 wherein the region of interest is less than or equal to the field of view in size.

8. A fluoroscopic imaging apparatus for enhancing, in real-time, a display of a region of interest within a fluoroscopic image, the apparatus comprising:
   an x-ray source for projecting x-rays through a subject, the x-ray source having a voltage and a current associated therewith for controlling the projected x-rays;
   an x-ray detector for detecting radiation which has passed from the x-ray source through the subject;
   display means for displaying real-time video images indicative of the detected radiation on a monitor;
   a pointing device by which an operator defines a region of interest during image acquisition from within the video images;
   an image processor for generating a histogram of image data of the region of interest;
   an automatic exposure controller for controlling at least one of the x-ray source voltage and the x-ray source current in response to the histogram of the region of interest; and
   an automatic brightness controller for mapping the image data of the region of interest to a display scale of the monitor in response to the histogram of the region of interest.

9. A fluoroscopic imaging apparatus according to claim 8 wherein the histogram is generated using all pixels from within the region of interest.

10. A fluoroscopic imaging apparatus according to claim 8 wherein the operator can interactively select the size and location of the region of interest using the pointing device.

11. A fluoroscopic imaging apparatus according to claim 10 wherein the pointing device has a position which is overlaid on the real-time video images displayed on the monitor.

12. A fluoroscopic imaging apparatus according to claim 8 wherein the display of the region of interest has a brightness range and the brightness range is substantially constant between successive displays of the region of interest.

13. A method of fluoroscopic imaging comprising the steps of:
   projecting x-rays through a subject using an x-ray source, the x-ray source having a voltage and current associated therewith;
   detecting radiation which has passed through the subject;
   displaying on a monitor an image indicative of the received radiation, the image defining a field of view;
   displaying borders of a region of interest, the region of interest being within the field of view and being defined by an operator during image acquisition and having a brightness and contrast associated therewith;
   generating a brightness histogram of the image data within the region of interest;
   adjusting at least one of the x-ray source voltage and current in response to the brightness histogram of the region of interest whereby the display of the region of interest is thereafter enhanced; and
   adjusting at least one of the brightness and contrast of the region of interest in response to the histogram of the region of interest whereby the display of the region of interest is thereafter enhanced.

14. A method of fluoroscopic imaging according to claim 13 wherein the step of generating a histogram includes using all pixels from within the region of interest.

15. A method of fluoroscopic imaging according to claim 13 wherein the step of adjusting at least one of the brightness and contrast of the region of interest includes mapping a minimum brightness from within the region of interest to black on the monitor and mapping a maximum brightness from within the region of interest to white on the monitor.

16. A method of fluoroscopic imaging according to claim 13 wherein the borders of the region of interest are superimposed on the display of the field of view.

17. A fluoroscopic imaging apparatus comprising:
   an x-ray source for projecting x-rays through a subject, the x-ray source having a voltage and a current associated therewith;
   an x-ray detector for detecting radiation which has passed through the subject;
   a monitor for displaying an image indicative of the detected radiation, the image defining a field of view;
   an operator interface for selecting a region of interest within the field of view; and
   enhancement means for enhancing, in response to image data within the region of interest, a subsequent image of the region of interest;
   wherein the operator interface includes a pointing device for selecting a size and a location of the region of interest and the position of the pointing device is overlaid on the image.

18. A fluoroscopic imaging apparatus for enhancing, in real-time, a display of a region of interest within a fluoroscopic image, the apparatus comprising:
   an x-ray source for projecting x-rays through a subject, the x-ray source having a voltage and a current associated therewith for controlling the projected x-rays;
   an x-ray detector for detecting radiation which has passed from the x-ray source through the subject,
   display means for displaying real-time video images indicative of the detected radiation on a monitor,
   a pointing device by which an operator can select a region of interest from within the video images;
   an image processor for generating a histogram of image data of the region of interest;
   an autonatic exposure controller for controlling at least one of the x-ray source voltage and the x-ray source current in response to the histogram of the region of interest; and
   an automatic brightness controller for mapping the image data of the region of interest to a display scale of the monitor in response to the histogram of the region of interest;
   wherein the operator can interactively select the size and location of the region of interest using the pointing device and the pointing device has a position which is overlaid on the real-time video images displayed on the monitor.

* * * * *